United States Patent
Huang et al.

(10) Patent No.: US 10,301,277 B2
(45) Date of Patent: May 28, 2019

(54) SUBSTITUTED UREAS AND METHODS OF TREATING MENTAL ILLNESS USING THE SAME

(71) Applicants: ZHEJIANG JINGXIN PHARMACEUTICAL CO., LTD., Zhejiang (CN); SHANGHAI JINGXIN BIOMEDICAL CO., LTD., Pudong Shanghai (CN); SHANGYU JINGXIN PHARMACEUTICAL CO., LTD., Shangyu, Zhejiang (CN)

(72) Inventors: Yue Huang, Shanghai (CN); Fei Zheng, Shanghai (CN)

(73) Assignees: ZHEJIANG JINGXIN PHARMACEUTICAL CO., LTD. (CN); SHANGHAI JINGXIN BIOMEDICAL CO., LTD. (CN); SHANGYU JINGXIN PHARMACEUTICAL CO., LTD. (CN)

( * ) Notice: Subject to any disclaimer, the term of this patent is extended or adjusted under 35 U.S.C. 154(b) by 0 days.

(21) Appl. No.: 15/759,119

(22) PCT Filed: Sep. 14, 2016

(86) PCT No.: PCT/CN2016/098953
§ 371 (c)(1),
(2) Date: Mar. 9, 2018

(87) PCT Pub. No.: WO2017/045599
PCT Pub. Date: Mar. 23, 2017

(65) Prior Publication Data
US 2018/0297975 A1 Oct. 18, 2018

(51) Int. Cl.
*C07C 275/26* (2006.01)
*C07D 333/54* (2006.01)
(Continued)

(52) U.S. Cl.
CPC .......... *C07D 333/54* (2013.01); *A61K 9/2013* (2013.01); *A61K 9/2018* (2013.01); *A61K 9/2054* (2013.01); *A61K 9/2059* (2013.01); *A61K 31/454* (2013.01); *A61K 31/496* (2013.01); *A61P 25/18* (2018.01); *C07D 261/20* (2013.01); *C07D 275/04* (2013.01); *C07D 333/72* (2013.01); *C07D 409/04* (2013.01);
(Continued)

(58) Field of Classification Search
CPC .................................................. C07C 275/26
USPC ........................................................ 564/57
See application file for complete search history.

(56) References Cited

U.S. PATENT DOCUMENTS 7,705,003 B2    4/2010    Csongor
7,825,123 B2    11/2010   Gobbi
(Continued)

FOREIGN PATENT DOCUMENTS

CN    101107236 A    1/2008
CN    101511805 A    8/2009
(Continued)

OTHER PUBLICATIONS

WIPO, International Search Report for International Application No. PCT/CN2016/098953, dated Dec. 13, 2016 (8 pages).

*Primary Examiner* — Douglas M Willis
(74) *Attorney, Agent, or Firm* — Haynes and Boone, LLP

(57) ABSTRACT

A cyclohexane derivative as shown by formula IB or a stereoisomer or a salt thereof, has a high affinity for $D_3$ receptors and 5-hydroxytryptamine, has a lower affinity for $D_2$ receptors, shows a high selectivity for $D_3/D_2$ receptors, and can be used as a therapeutic drug against neuropsychiatric diseases.

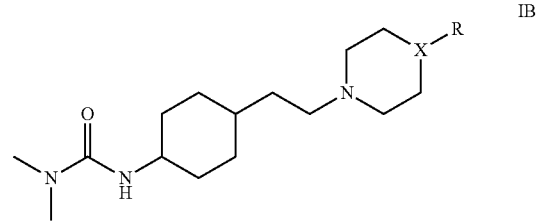

wherein; X is N or CH; R is

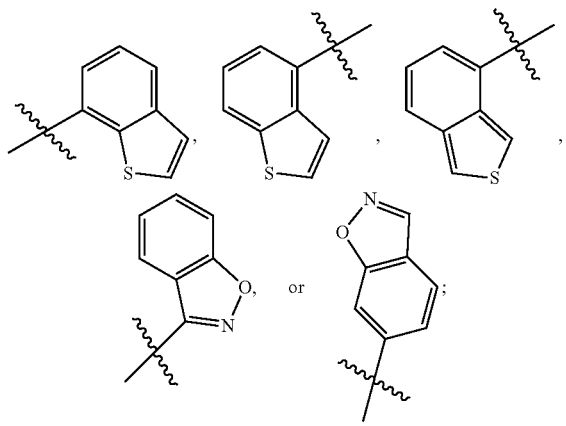

R is optionally substituted with one or more substituents selected from the group consisting of F, Cl, Br, I and $C_1$-$C_6$ (Continued)

alkyl; and the $C_1$-$C_6$ alkyl is optionally substituted with one or more substituents selected from the group consisting of F, Cl, Br, and I.

27 Claims, No Drawings

(51) Int. Cl.

| | |
|---|---|
| *C07D 333/72* | (2006.01) |
| *C07D 413/04* | (2006.01) |
| *A61P 25/18* | (2006.01) |
| *A61K 9/20* | (2006.01) |
| *A61K 31/454* | (2006.01) |
| *A61K 31/496* | (2006.01) |
| *C07D 261/20* | (2006.01) |
| *C07D 409/04* | (2006.01) |
| *C07D 417/04* | (2006.01) |
| *C07D 275/04* | (2006.01) |

(52) U.S. Cl.
CPC ......... *C07D 413/04* (2013.01); *C07D 417/04* (2013.01)

(56) References Cited

U.S. PATENT DOCUMENTS

| | | |
|---|---|---|
| 7,858,630 B2 | 12/2010 | Gobbi |
| 7,939,535 B2 | 5/2011 | Gobbi |
| 8,470,828 B2 | 6/2013 | Gobbi |
| 8,802,678 B2 | 8/2014 | Capet |
| 8,829,029 B2 | 9/2014 | Gobbi |

FOREIGN PATENT DOCUMENTS

| | | |
|---|---|---|
| CN | 101778844 A | 7/2010 |
| CN | 102159557 A | 8/2011 |
| CN | 102164914 A | 8/2011 |
| CN | 102164927 A | 8/2011 |
| CN | 102958936 A | 3/2013 |
| CN | 103130737 A | 6/2013 |
| CN | 104140421 A | 11/2014 |

SUBSTITUTED UREAS AND METHODS OF TREATING MENTAL ILLNESS USING THE SAME

CROSS-REFERENCE TO RELATED APPLICATIONS

This application is a national stage entry of PCT/CN2016/098953 filed Sep. 14, 2016, which claims priority to Chinese Patent Application No. 201510582267.0 filed Sep. 15, 2015 and Chinese Patent Application No. 201610643389.0 filed Aug. 8, 2016, the contents of each of which are incorporated herein in their entirety by express reference thereto.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present application relates to medicinal chemistry, in particular to cyclohexane compounds or stereoisomers or salts thereof, and more particularly to cyclohexane derivatives of formula IB or formula I, or stereoisomers or salts thereof, and preparation and use thereof.

Description of Related Art

Mental disorders have been the diseases that seriously affect human health with the rapid social development, the increased pace and stress from lives, which leads to bad consequences for the patients and their families. Suicide, deficiency of medical care and high risk of complications (for example, malnutrition, insufficient exercises, obesity and smoking) are contributors to shortened average life expectancy of patients. Many studies have shown that mental disorders are associated with various neurotransmitters and receptor dysfunction in the central nervous system; for example, monoamine neurotransmitters in brain, especially dopamine (DA) system and 5-hydroxytryptamine (5-HT) system are closely related to the normal mental activities. Dysfunction of DA and 5-HT systems can lead to a variety of neuropsychiatric diseases, such as schizophrenia, depression, neuropathic pain, mania, anxiety and Parkinson's disease.

The Patent WO 9967206 A1 discloses an application of a cyclohexane derivative in the treatment of pain diseases, but is silent about the application in mental diseases, especially for dopamine $D_2/D_3$ receptors.

The Patent CN 1829703 A discloses an application of a cyclohexane derivative having (thio) carbamoyl side chain in the modulation of dopamine receptor-related disorders, in which the $D_2/D_3$ antagonist and 5-$HT_{1A}$ partial agonist Cariprazine (Cariprazine, RGH-188) jointly developed by Forest Laboratories and Gedeon Richter for the treatment of schizophrenia, mania and depression have now passed clinical trials and entered the registration and approval stage. Cariprazine has a formula as shown below, and has affinities (Ki values) of 0.72 nmol, 0.08 nmol and 3.42 nmol for $D_2/D_3$ receptors and 5-$HT_{1A}$, respectively, i.e. it does have a certain selectivity to D2/D3 receptor, but still not ideal. It is therefore possible that such drug clinically has less chance (nearly 5% probability at a dose of 3 mg) on the occurrence of the cathisophobia, extrapyramidal reaction as these side effects are associated with excessive blocking of the $D_2$ receptor.

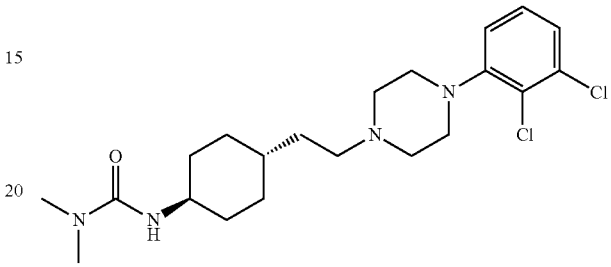

In light of the above problems, Cariprazine is further structurally modified in Patent CN 103130737 A so as to achieve higher selectivity to the $D_3$ receptor.

However, given the various causes for mental diseases, there remains a need for the development of the medicaments to meet the requirement from the treatment of mental diseases, although the compounds as described above function well against schizophrenia.

BRIEF SUMMARY OF THE INVENTION

BRIEF DESCRIPTION OF THE SEVERAL VIEWS OF THE DRAWING(S)

Not Applicable

The technical problem to be solved in the present invention is to overcome the above shortcomings, to study, design and improve the cyclohexane derivative structure. The present application provides a cyclohexane derivative of formula IB and formula I, or a stereoisomer or a salt thereof, which produces $D_2/D_3$ antagonism and 5-hydroxytryptamine absorption inhibition, as well as anti-schizophrenia effect, thus increasing the spectrum of mental illness treatment and reducing side effects.

The present invention provides a cyclohexane derivative of formula IB, or a stereoisomer or salt thereof:

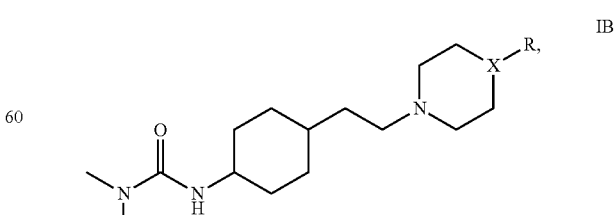

wherein X is N or C;

R is

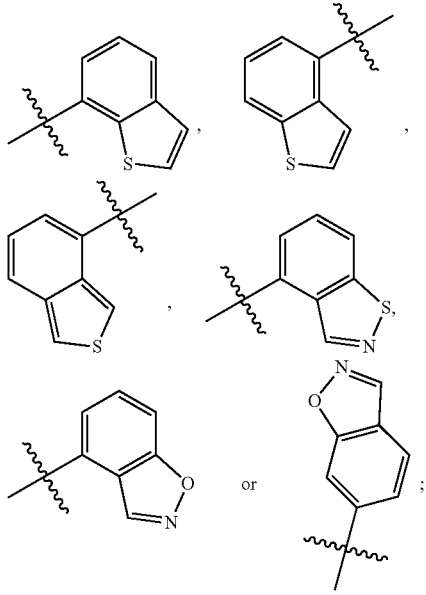

and R group is optionally substituted with one or more substituents selected from halogen, substituted or unsubstituted $C_1$-$C_6$ alkyl; the halogen is selected from one or more of F, Cl, Br or I; the substituted or unsubstituted $C_1$-$C_6$ alkyl is selected from a substituted or unsubstituted $C_1$-$C_4$ alkyl, for example methyl, ethyl, propyl or butyl; the substituent is halogen, for example one or more of F, Cl, Br or I; and the substituted $C_1$-$C_4$ alkyl is preferably trifluoromethyl.

Preferably, the present invention provides a cyclohexane derivative of formula I, or a stereoisomer or salt thereof:

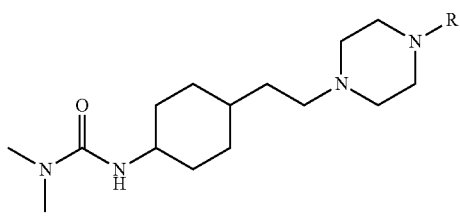

I wherein R is

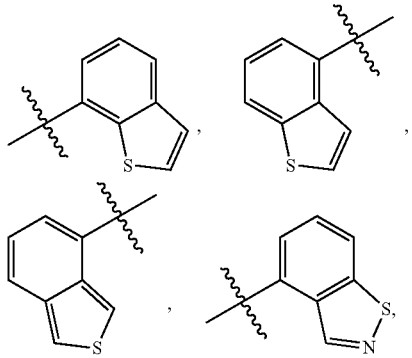

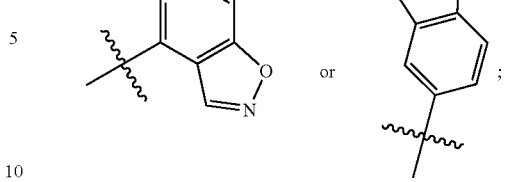

and R group is optionally substituted with one or more substituents selected from halogen, substituted or unsubstituted $C_1$-$C_6$ alkyl; the halogen is selected from one or more of F, Cl, Br or I; the substituted or unsubstituted $C_1$-$C_6$ alkyl is selected from a substituted or unsubstituted $C_1$-$C_4$ alkyl, for example methyl, ethyl, propyl or butyl; the substituent is halogen, for example one or more of F, Cl, Br or I; and the substituted $C_1$-$C_4$ alkyl is preferably trifluoromethyl.

The stereoisomer of the cyclohexane derivative of the present invention is a cis-stereoisomer or a trans-stereoisomer, preferably a trans-stereoisomer.

The salt of the cyclohexane derivative of the present invention is formed from a cyclohexane derivative with an acid which is an organic or inorganic acid, wherein the inorganic acid is selected from hydrochloric acid, sulfuric acid, nitric acid or phosphoric acid; the organic acid is selected from formic acid, acetic acid, oxalic acid, malonic acid, maleic acid, fumaric acid, succinic acid or benzoic acid; and other physiologically acceptable salt.

Preferably, the cyclohexane derivative or a stereoisomer or salt thereof is selected from the following compounds or salts thereof:

N'-[trans-4-[2-[4-(benzo[b]thiophene)-7-piperazinyl]ethyl] cyclohexyl]-N,N-dimethylurea (compound 1);

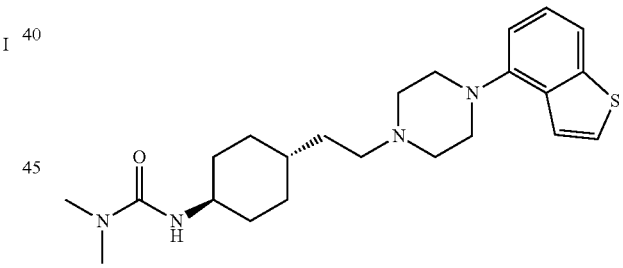

1

N'-[trans-4-[2-[7-(benzo[b]thiophene)-7-piperazinyl]ethyl] cyclohexyl]-N,N-dimethylurea (compound 2);

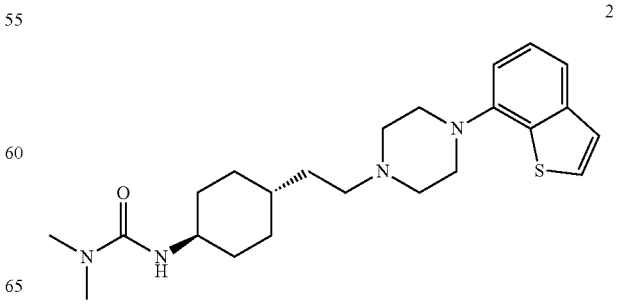

2

N'-[trans-4-[2-[4-(benzo[c]thiophene)-7-piperazinyl]ethyl]cyclohexyl]-N,N-dimethylurea (compound 3);

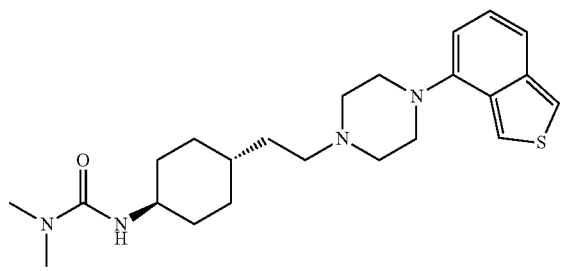

N'-[trans-4-[2-[4-(benzo[d]isothiazolyl)-3-piperazinyl]ethyl]cyclohexyl]-N,N-dimethylurea (compound 4);

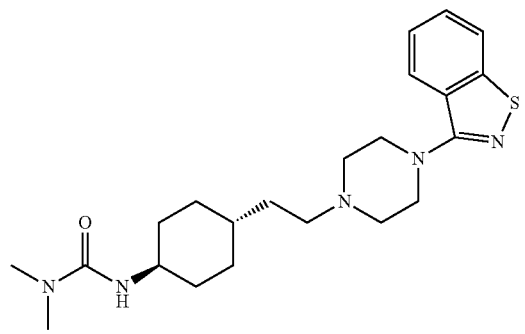

N'-[trans-4-[2-[4-(6-fluoro-benzo[d]isoxazol)-3-piperazinyl]ethyl]cyclohexyl]-N,N-dimethylurea (compound 5);

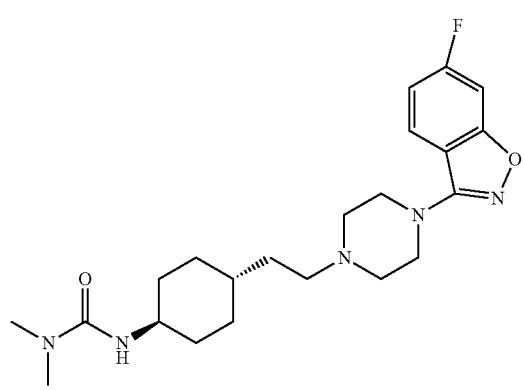

N'-[trans-4-[2-[4-(3-chloro-benzo[d]isoxazol)-6-piperazinyl]ethyl]cyclohexyl]-N,N-dimethylurea (compound 6);

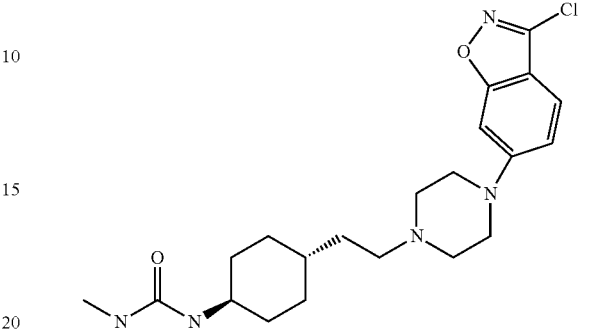

N'-[trans-4-[2-[4-(6-fluoro-benzo[d]isoxazol)-3-piperidyl]ethyl]cyclohexyl]-N,N-dimethylurea (compound 7);

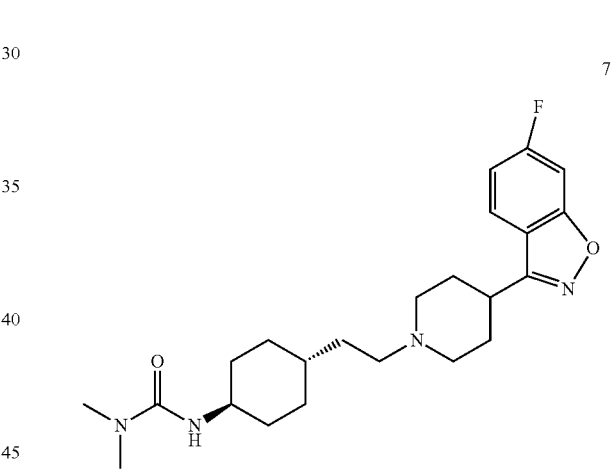

N'-[trans-4-[2-[4-(benzo[b]thiophene)-7-piperidinyl]ethyl]cyclohexyl]-N,N-dimethylurea (compound 8);

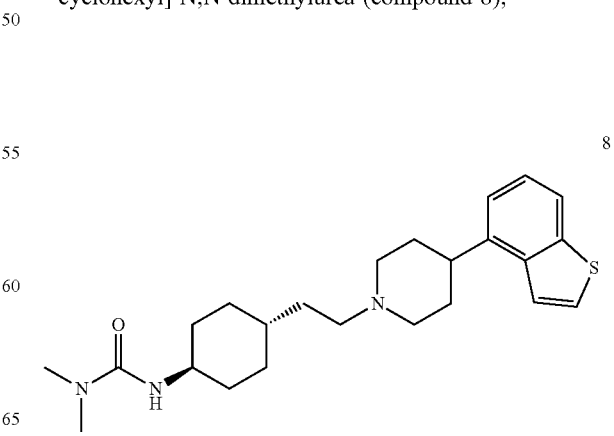

N'-[trans-4-[2-[7-(benzo[b]thiophene)-7-piperidinyl]ethyl]
cyclohexyl]-N,N-dimethylurea (compound 9);

N'-[trans-4-[2-[4-(3-chloro-benzo[d]isoxazol)-6-piperidi-
nyl]ethyl]cyclohexyl]-N,N-dimethylurea (compound 12);

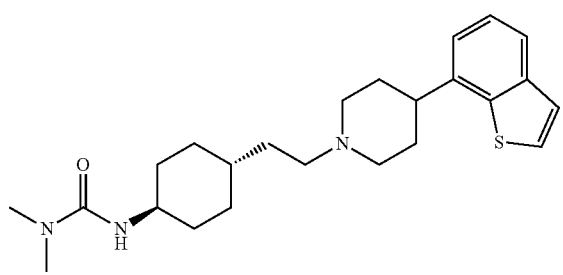

N'-[trans-4-[2-[4-(benzo[c]thiophene)-7-piperidinyl]ethyl]
cyclohexyl]-N,N-dimethylurea (compound 10);

N'-[trans-4-[2-[4-(3-methyl-benzo[d]isoxazol)-6-piperazi-
nyl]ethyl]cyclohexyl]-N,N-dimethylurea (compound 13);

N'-[trans-4-[2-[4-(benzo[d]isothiazolyl)-3-piperidinyl]
ethyl]cyclohexyl]-N,N-dimethylurea (compound 11);

N'-[trans-4-[2-[4-(6-methyl-benzo[d]isoxazol)-4-piperazi-
nyl]ethyl]cyclohexyl]-N,N-dimethylurea (compound 14).

On the other hand, the present invention provides a method for preparing the cyclohexane derivative or stereoisomer or salt thereof, which comprises following steps:

reacting 4-ethylcyclohexylamine derivative II with N,N-dimethylcarbamyl chloride III in the presence of an acid-binding reagent to produce the compound IB:

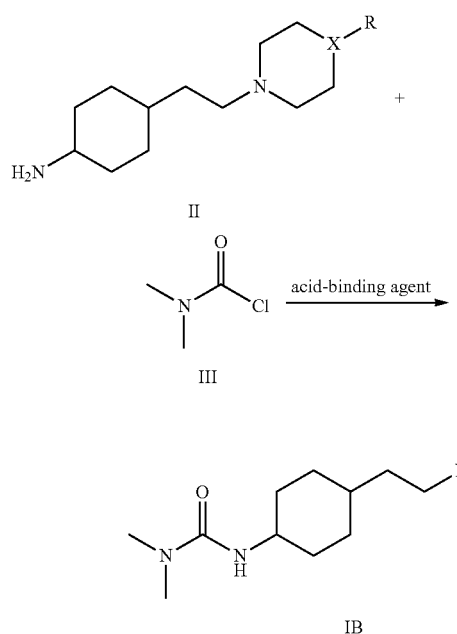

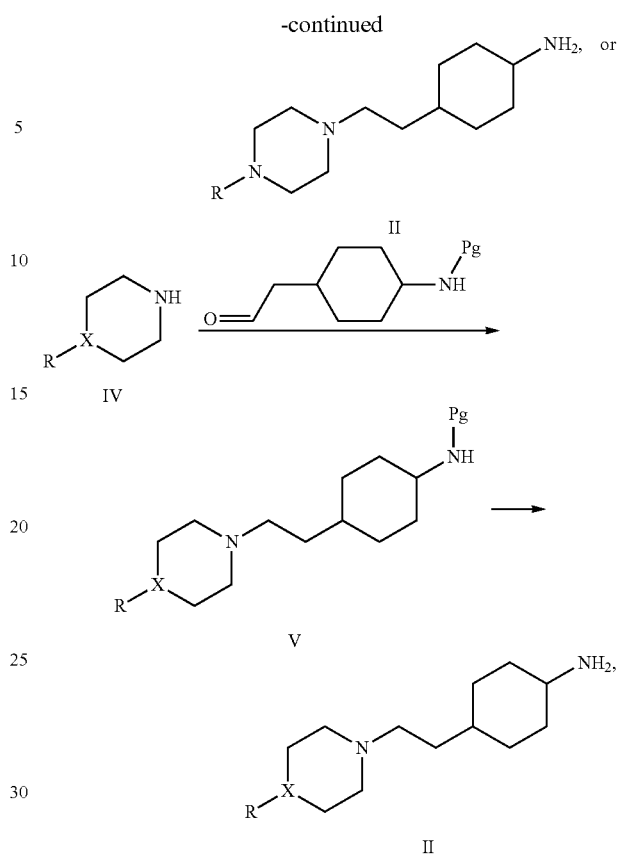

wherein R and X are as defined above.

The molar ratio of the compound II to the compound III is 1-1.5:1, the reaction temperature is 0° C.-50° C., the acid-binding agent is an organic base selected from one or more of triethylamine, diisopropylethylamine or pyridine, or an inorganic base selected from one or more of sodium carbonate, potassium carbonate, sodium bicarbonate or potassium bicarbonate; and the molar ratio of the acid-binding agent (alkaline substance) to the compound II is 1-1.5:1.

The present invention further provides a method for preparing the compound II, which comprises following steps:

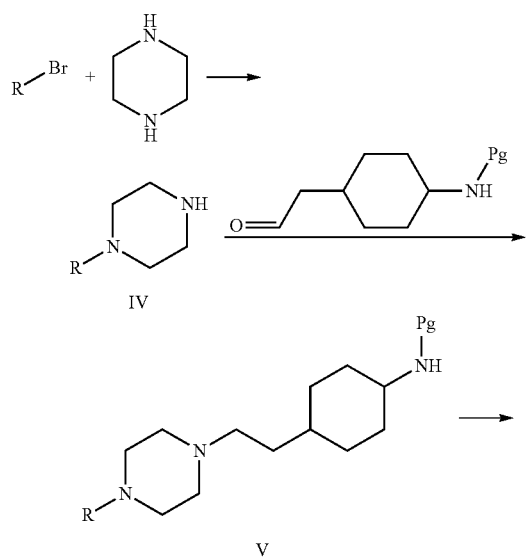

wherein R and X are as defined above, and Pg is an amino-protecting group selected from benzyl (Bn), benzyl formate (CBz) or t-butyloxycarbonyl (Boc). The compound of formula II may be cis- or trans-; optionally, the cis- or trans-stereoisomers may be obtained by subjecting the compound of formula IB to chromatography separating or crystallizing.

i) when X is N, coupling piperazine with bromide to produce an intermediate IV;
   wherein the coupling reaction is carried out in the presences of palladium catalyst and a strong alkali selected from potassium tert-butoxide, sodium tert-butoxide, potassium carbonate or cesium carbonate, the reaction temperature is 50-150° C., and the molar ratio of piperazine to the bromide is 1-5:1; or
when X is C, the intermediate IV is commercially available (Shanghai Excellent Chemical Co, Ltd.).

ii) subjecting the intermediate IV and 4-amino-protected cyclohexaneacetaldehyde to a condensation and imine reduction reaction to produce an intermediate V;
   wherein a reducing agent used is a boron compound such as sodium triacetoxyborohydride or sodium borohydride; the feeding molar ratio of the intermediate IV to the 4-amino-protected cyclohexaneacetaldehyde is 1-1.2:1; the molar ratio of the boron compound to the intermediate IV is 1-2:1; and iii) removing the amino-protecting group;
   in more particular, when Pg is t-butyloxy carbonyl (Boc), removing the amino-protecting group by using an acid which is a hydrogen chloride organic solution, or trifluoroacetic acid, etc.; or when Pg is benzyl (Bn) or benzyl formate (CBz), removing the amino-protecting group by hydrogenation using palladium-on-carbon catalyst at a hydrogenation pressure of 0.1-1 Mpa.

The present invention also provides a use of the cyclohexane derivatives or stereoisomers or salts thereof in preparing a drug against neuropsychiatric diseases.

The cyclohexane derivatives or stereoisomers or salts thereof according to the present invention are new compounds. These compounds are produced with pharmacophore fusion-based drug design; particularly, pharmacophore which potentially acts on the dopamine $D_3$ receptor and pharmacophore that has a potential inhibition on 5-hydroxytryptamine absorption are fused, and then the compounds are structurally modified and prepared, followed by in vitro test on biological activity and in vivo test on anti-schizophrenic activity, study on structure-activity relationship and optimization. The pharmacological results show that the cyclohexane derivatives or stereoisomers or salts thereof according to the present invention have higher affinity to the $D_3$ receptor and 5-hydroxytryptamine, but have lower affinity to the $D_2$ receptor, demonstrating a high selectivity for $D_3/D_2$ receptors, and achieving an unexpected effect. The in vitro receptor binding assay indicates that most of the cyclohexane derivatives or stereoisomers or salts thereof show strong affinity (Ki<10 nmol) to dopamine $D_3$ receptor and 5-$HT_{1A}$ receptor and weak affinity to dopamine $D_2$ receptor (Ki>50 nmol), demonstrating excellent selectivity for $D_3/D_2$ receptors and strong affinity to 5-$HT_{1A}$ receptor. The in vivo test on anti-schizophrenic activity shows that the cyclohexane derivatives or stereoisomers or salts thereof function well on schizophrenia. The study on structure-activity relationship shows that the strong affinity to $D_3/D_2$ and 5-$HT_{1A}$ receptors and high selectivity to $D_3/D_2$ receptors, as well as the anti-schizophrenia effect are closely linked to the benzoheterocycle fragments such as benzothiophene, benzisothiazole or benzisoxazole in a series of cyclohexane derivatives according to the present invention (in the prior art the corresponding fragment of Cariprazine is 2,3-dichlorobenzene).

Therefore, the cyclohexane derivatives or stereoisomers or salts thereof according to the present invention can be used in preparing a drug against neuropsychiatric diseases.

The drug of the present invention is a pharmaceutical composition consisting of the cyclohexane derivative or stereoisomer or salt thereof as an active ingredient and a pharmaceutical excipient.

The pharmaceutical composition of the present invention may be administered in any convenient manner, for example, oral, gastrointestinal, buccal, sublingual, nasal, rectal or transdermal. The pharmaceutical composition may be made into different forms such as solid and liquid preparations, for example suspensions, tablets and capsules.

The composition in the form of a tablet may include fillers, lubricants, adhesives and disintegrants conventionally used in preparations. Liquid preparations are prepared by using a suitable liquid carrier, such as a water-soluble solvent, e.g., water, ethanol or glycerol, or a water-insoluble solvent e.g., polyethylene glycol, or a suspension or solution in the oil.

Particularly, the pharmaceutical composition is a solid tablet consisting of the cyclohexane derivative of formula IB or formula I or stereoisomer or salt thereof as an active ingredient and a pharmaceutical excipient.

The solid tablet consists of the following components based on weight:
active ingredient: 1-40 mg
diluent: 10-200 mg
adhesive: 5-25 mg
disintegrant: 5-50 mg and
lubricant: 1-5 mg;
wherein the diluent is selected from starch, lactose or microcrystalline cellulose; the adhesive is selected from hydroxybenzyl cellulose, hydroxypropylmethyl cellulose or polyvinylpyrrolidone;
the disintegrant is selected from sodium hydroxyethyl starch or crospovidone; and the lubricant is magnesium stearate.

Preferably, the pharmaceutical composition is a solid tablet consisting of N'-[trans-4-[2-[4-(benzo[b]thiophene)-7-piperazinyl]ethyl]cyclohexyl]-N,N-dimethylurea as an active ingredient and a pharmaceutical excipient.

The solid tablet consists of the following components based on weight:
active ingredient: 1-40 mg
diluent: 10-200 mg
adhesive: 5-25 mg
disintegrant: 5-50 mg and
lubricant: 1-5 mg;
wherein the diluent is selected from starch, lactose or microcrystalline cellulose; the adhesive is selected from hydroxybenzyl cellulose, hydroxypropylmethyl cellulose or polyvinylpyrrolidone; the disintegrant is selected from sodium hydroxyethyl starch or crospovidone; and the lubricant is magnesium stearate.

Alternatively, the pharmaceutical composition is a suspension consisting of the cyclohexane derivative of formula IB or formula I or stereoisomer or salt thereof as an active ingredient and a pharmaceutical excipient.

The suspension consists of the following components based on weight:
active ingredient: 1-40 mg
diluent: 10-200 mg
suspending agent: 0.1-10 mg
preservative: 0.01-0.5 mg
buffer: 4-8 mg
co-solvent: 0-50 mg
flavoring agent: 0-1 mg and
colorant: 0-0.1 mg;
wherein the suspending agent is selected from xanthan gum or microcrystalline cellulose; the preservative is selected from sodium benzoate, methyl or ethyl p-hydroxybenzoate; the diluent is selected from water or sorbitol; the buffer is citrate; the co-solvent is selected from cyclodextrin, ethanol, propylene glycol or polyethylene glycol; the flavoring agent can be a sweetener known to the person skilled in the art (e.g., sugar or saccharin, etc.); the colorant can be a fat-soluble or water-soluble colorant, such as carotene, cocoa pigment or caramel pigment, etc.

Preferably, the present invention provides a suspension consisting of N'-[trans-4-[2-[4-(benzo[b]thiophene)-7-piperazinyl]ethyl]cyclohexyl]-N,N-dimethylurea as an active ingredient and a pharmaceutical excipient.

The suspension consists of the following components based on weight:
active ingredient: 1-40 mg
diluent: 10-200 mg
suspending agent: 0.1-10 mg
preservative: 0.01-0.5 mg
buffer: 4-8 mg
co-solvent: 0-50 mg
flavoring agent: 0-1 mg and
colorant: 0-0.1 mg;
wherein the suspending agent is selected from xanthan gum or microcrystalline cellulose; the preservative is selected from sodium benzoate, methyl or ethyl p-hydroxybenzoate;

the diluent is selected from water or sorbitol; the buffer is citrate; the co-solvent is selected from cyclodextrin, ethanol, propylene glycol or polyethylene glycol; the flavoring agent can be a sweetener known to the person skilled in the art (e.g., sugar or saccharin, etc.); the colorant is a fat-soluble or water-soluble colorant, such as carotene, cocoa pigment or caramel pigment, etc.

The present invention further provides a use of the cyclohexane derivatives or stereoisomers or salts thereof in preparing a drug against neuropsychiatric diseases; and the use refers to the use of the cyclohexane derivatives or stereoisomers or salts thereof in preparing a drug for improving/treating schizophrenia, mental disorders, dysphrenia, mental confusion, mood disorders, bipolar disorders, depression, phobia, obsessive-compulsive disorders, anxiety and cognitive disorders.

An acute toxicity experiment shows that the cyclohexane derivatives of the present invention or stereoisomers or salts thereof have very low toxicity ($LD_{50}$>1,000 mg/Kg), which are significantly superior to Cariprazine ($LD_{50}$=75.3 mg/Kg), indicating that the drug of the present invention is less toxic and safe.

A pharmacological test shows that the cyclohexane derivatives of the present invention or stereoisomers or salts thereof are novel therapeutic drugs against neuropsychiatric disorders and have good prospects on clinical application, which would be good news for patients and bring good social benefits. In addition, the method for preparing the compound of the present invention is simple and easy to operate, suitable for industrial production and valuable.

DETAILED DESCRIPTION OF THE INVENTION

Materials and agents used in the following examples are commercially available, unless otherwise specified.

EXAMPLE 1

Preparation of 1-benzo[b]thiophene-4-piperazine hydrochloride

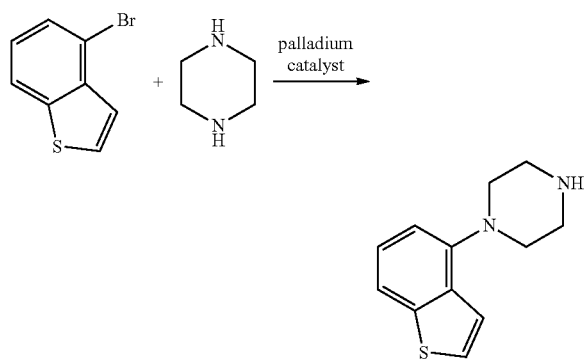

A mixture of 7.20 g of 4-bromobenzo[b]thiophene, 19.9 g of piperazine anhydride, 4.70 g of sodium tert-butoxide, 0.32 g of (R)-(+)-2,2'-bis(diphenylphosphino)-1,1'-dinaphthalene (BINAP), 0.63 g of tris(dibenzylideneacetone)dipalladium and 150 ml of toluene was refluxed at nitrogen atmosphere for 1 hour. 150 ml of water was added to the mixture, extracted with 100 ml×3 of ethyl acetate, washed with water, dried with magnesium sulfate and then evaporated under reduced pressure to remove the solvent (0.01 MPa, 45° C.). The remainder was purified by silica gel column chromatography (methylene chloride:methanol: 25% aqueous ammonia=100:10:1) to obtain 4.60 g of 1-benzo[b]thiophen-4-yl-piperazine as a yellow oil. 2 ml of concentrated hydrochloric acid was added to a methanol solution (25 ml) containing 4.6 g of 1-benzo[b]thiophen-4-yl-piperazine, and evaporated under reduced pressure (0.01 MPa, 45° C.) to remove the solvent. Ethyl acetate (50 ml) was added to the remainder to precipitate and crystallize. The resultant was filtered and then dissolved in 15 ml of methanol under reflux. After cooling to room temperature (25° C.), recrystallization was carried out to give the crystallized 1-benzo[b]thiophene-4-yl-piperazine hydrochloride as colorless needles.

EXAMPLE 2

Preparation of trans-4-[2-[4-(benzo[b]thiophen)-7-piperazinyl]ethyl]cyclohexyl-tert-butyl carbamate

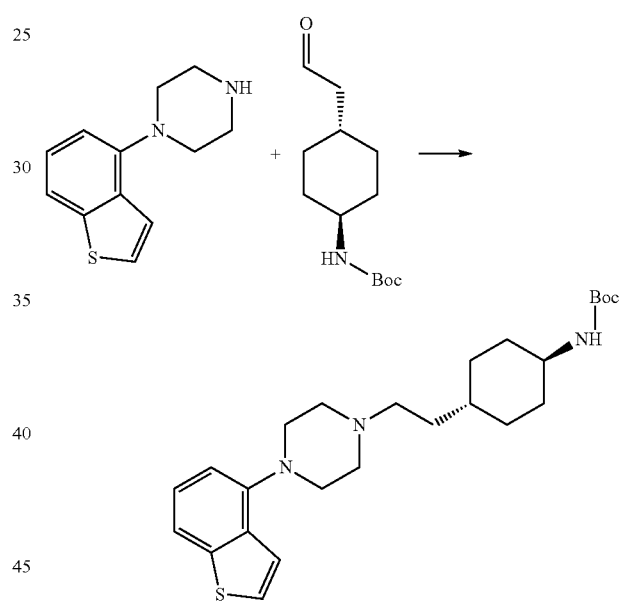

2.54 g (10 mmol) of 1-benzo[b]thiophene-4-piperazine hydrochloride prepared in Example 1 and 2.40 g (10 mmol) of trans-2-{1-[4-(N-tert-butoxycarbony)amino]cyclohexyl}-acetaldehyde were dissolved in 120 ml of dichloromethane. 1.40 ml (10 mmol) of triethylamine was added slowly at room temperature (25° C.±2° C.), stirred for 10 minutes, and then 3.16 g (14.8 mmol) of sodium triacetoxyborohydride was added gradually. The mixture was stirred at room temperature for reaction for 24 hours. After the reaction was completed, 120 ml of 10% sodium bicarbonate solution was added. The reaction system was directly extracted and separated, the organic phase was dried with anhydrous sodium sulfate, and filtered and evaporated to dryness. The solid was refluxed to dissolve with 15 ml of ethyl acetate, and then cooled to room temperature (25° C.±2° C.), crystallized to give 3.70 g of the desired product.

$^1$H-NMR (CDCl$_3$) δ ppm: 7.81 (1H, brs), 7.78 (1H, d, J=5.5 Hz), 7.73 (1H, d, J=8.1 Hz), 7.41 (1H, m), 7.30 (1H, d, 7.6 Hz), 6.94 (1H, d, J=7.6 Hz), 3.54 (1H, m), 3.35-3.23

(8H, m), 2.46 (2H, m), 1.86-1.65 (8H, m), 1.51-1.49 (1H, m), 1.42 (9H, s), 1.37-1.35 (2H, m).

EXAMPLE 3

Preparation of trans-4-[2-[4-(benzo[b]thiophene)-7-piperazinyl]ethyl]cyclohexylamine

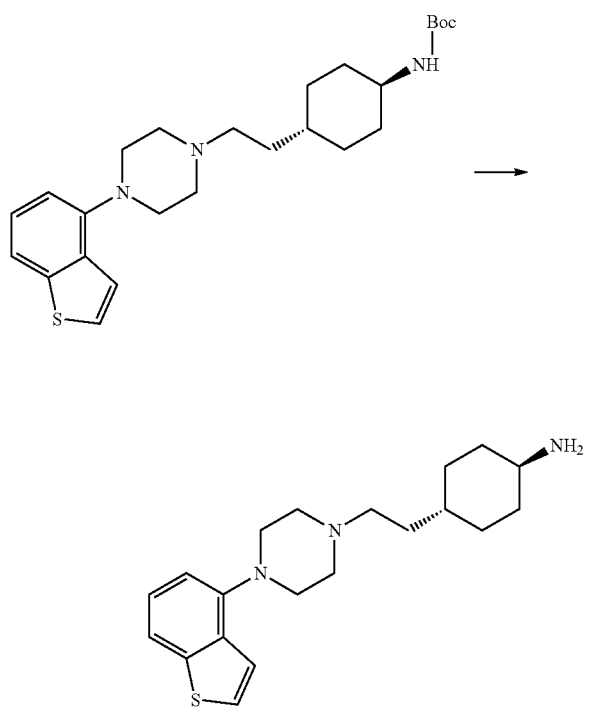 [SMILES: CC(C)(C)OC(=O)N[C@H]1CC[C@H](CCN2CCN(c3cccc4sccc34)CC2)CC1 ; N[C@H]1CC[C@H](CCN2CCN(c3cccc4sccc34)CC2)CC1]

4.43 g of trans-4-[2-[4-(benzo[b]thiophen)-7-piperazinyl]ethyl]cyclohexyl-tert-butyl carbamate prepared in Example 2 was placed in a reaction flask under an ice-water bath. 80 ml of a saturated solution of hydrogen chloride in ethyl acetate was added to the reaction flask. The reaction was stirred for 8 hours for de-protection and finally a white precipitate was formed to give 3.42 g of the hydrochloride of the desired product. The resulting solid was added to 50 ml of dichloromethane solution, and then 50 ml of a saturated solution of sodium bicarbonate was added, stirred for 0.5 hour. This mixture was extracted and separated and the organic phase was concentrated (0.01 MPa, 40° C.) to give 3.30 g of the desired product.

$^1$H-NMR (CDCl$_3$) δ ppm: 7.78 (1H, d, J=5.5 Hz), 7.76 (1H, d, J=8.1 Hz), 7.37 (1H, m), 7.29 (1H, d, 7.6 Hz), 6.96 (1H, d, J=7.6 Hz), 3.48-3.38 (8H, m), 2.53 (1H, m), 2.46 (2H, m), 1.78-1.63 (8H, m), 1.51-1.49 (1H, m), 1.42 (2H, brs), 1.37-1.35 (2H, m).

EXAMPLE 4

Preparation of N'-[trans-4-[2-[4-(benzo[b]thiophene)-7-piperazinyl]ethyl]cyclohexyl]-N,N-dimethylurea (Compound 1)

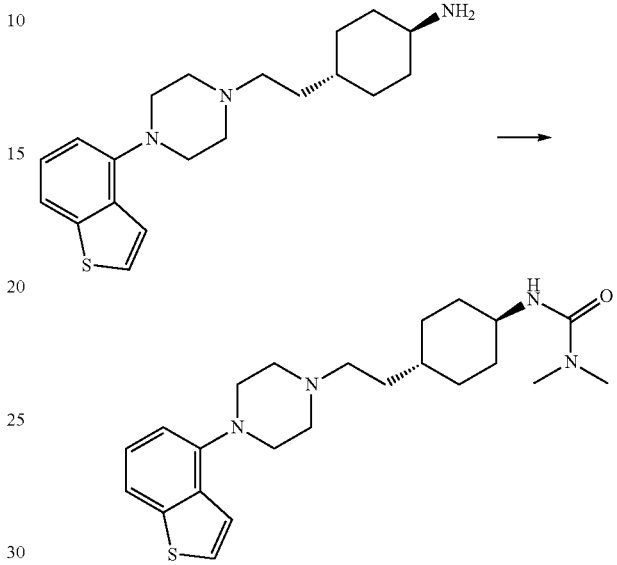

1.73 g of trans-4-[2-[4-(benzo[b]thiophene)-7-piperazinyl]ethyl]cyclohexylamine prepared in Example 3 was dissolved in 50 ml of dichloromethane. 1.40 ml of triethylamine was added, and then 5.50 mmol of N,N-dimethylcarbamyl chloride was added. The mixture was stirring for 48 hours at room temperature (25° C.±2° C.). After the reaction was completed, 50 ml of water was added to extract and separate the reactant. The organic phase was concentrated (0.01 MPa, 45° C.) and the desired component was collected by using column chromatography of methanol:dichloromethane=1:10 (400 mesh silica gel) and then concentrated to give 1.89 g of the amorphous desired product.

$^1$H-NMR (CDCl$_3$) δ ppm: 7.79 (1H, d, J=5.5 Hz), 7.76 (1H, d, J=8.1 Hz), 7.33 (1H, m), 7.28 (1H, d, 7.6 Hz), 6.96 (1H, d, J=7.6 Hz), 6.48 (1H, brs), 3.44-3.36 (8H, m), 3.58 (1H, m), 3.01 (6H, s), 2.46 (2H, m), 1.68-1.42 (8H, m), 1.52-1.48 (1H, m), 1.38-1.36 (2H, m).

EXAMPLE 5

Preparation of N'-[trans-4-[2-[7-(benzo[b]thiophene)-7-piperazinyl]ethyl]cyclohexyl]-N,N-dimethylurea (Compound 2)

Compound 2 was prepared according to the procedures given in Examples 1-4 by using 7-bromobenzo[b]thiophene as a starting material.

$^1$H-NMR (CDCl$_3$) δ ppm: 7.78 (1H, d, J=5.6 Hz), 7.76 (1H, d, J=8.0 Hz), 7.31 (1H, m), 7.27 (1H, d, 7.6 Hz), 6.98 (1H, d, J=7.2 Hz), 6.44 (1H, brs), 3.48-3.42 (8H, m), 3.54 (1H, m), 3.00 (6H, s), 2.46 (2H, m), 1.68-1.42 (8H, m), 1.52-1.48 (1H, m), 1.38-1.36 (2H, m).

EXAMPLE 6

Preparation of N'-[trans-4-[2-[4-(benzo[c]thiophene)-7-piperazinyl]ethyl]cyclohexyl]-N,N-dimethylurea (Compound 3)

Compound 3 was prepared according to the procedures given in Examples 1-4 by using 4-bromobenzo[c]thiophene as a starting material.

$^1$H-NMR (CDCl$_3$) δ ppm: 7.33 (2H, s), 7.27-7.25 (1H, m), 7.27 (1H, d, 7.6 Hz), 6.77 (1H, d, J=7.2 Hz), 6.73 (1H, d, J=7.2 Hz), 6.44 (1H, brs), 3.48-3.42 (8H, m), 3.54 (1H, m), 2.99 (6H, s), 2.46 (2H, m), 1.68-1.42 (8H, m), 1.52-1.48 (1H, m), 1.46-1.42 (2H, m).

EXAMPLE 7

Preparation of N'-[trans-4-[2-[4-(6-fluoro-benzo[d]isoxazol)-3-piperazinyl]ethyl]cyclohexyl]-N,N-dimethylurea (compound 5)

Compound 5 was prepared according to the procedures given in Examples 1-4 by using 6-fluoro-3-bromo-1,2 benzo[d]isoxazole as a starting material.

$^1$H-NMR (CDCl$_3$) δ ppm: 7.41 (1H, d), 7.12 (1H, d), 6.98 (1H, s), 6.52 (1H, brs), 3.55 (1H, m), 3.46-3.42 (8H, m), 2.99 (6H, s), 2.45 (2H, m), 1.68-1.40 (8H, m), 1.50-1.48 (1H, m), 1.37-1.35 (2H, m).

EXAMPLE 8

Preparation of N'-[trans-4-[2-[4-(3-chloro-benzo[d]isoxazol)-6-piperazinyl]ethyl]cyclohexyl]-N,N-dimethylurea (Compound 6)

Compound 6 was prepared according to the procedures given in Examples 1-4 by using 3-chloro-6-bromo-benzo[d]isoxazole as a starting material.

$^1$H-NMR (CDCl$_3$) δ ppm: 7.25 (1H, d), 6.78 (1H, s), 6.72 (1H, d), 6.51 (1H, brs), 3.54 (1H, m), 3.46-3.42 (8H, m), 2.99 (6H, s), 2.45 (2H, m), 1.67-1.40 (8H, m), 1.50-1.48 (1H, m), 1.42-1.35 (2H, m).

EXAMPLE 9

Preparation of N'-[trans-4-[2-[4-(6-fluoro-benzo[d]isoxazol)-3-piperidyl]ethyl]cyclohexyl]-N,N-dimethylurea (Compound 7)

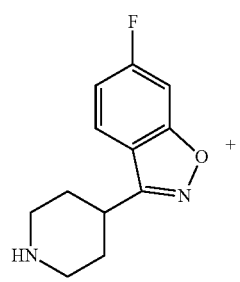

+

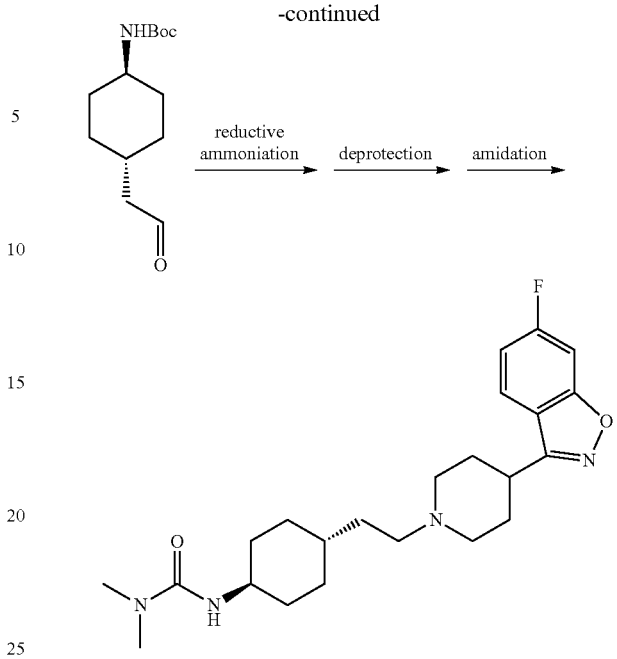

Compound 7 was prepared according to the procedures given in Examples 2-4 by using 6-fluoro-3-piperidin-4-yl-1,2 benzo[d]isoxazole (available from Shanghai Excellent Chemical Co., Ltd.) as a starting material.

$^1$H-NMR (CDCl$_3$) δ ppm: 7.41 (1H, d), 7.12 (1H, d), 6.97 (1H, s), 6.51 (1H, brs), 3.55-3.53 (1H, m), 2.99 (6H, s), 2.78-2.76 (1H, m), 2.66-2.37 (4H, m), 2.46-2.40 (2H, m), 1.78-1.68 (12H, m), 1.50-1.48 (1H, m), 1.37-1.34 (2H, m).

EXAMPLE 10

Preparation of solid tablets of N'-[trans-4-[2-[4-(benzo[b]thiophene)-7-piperazinyl]ethyl]cyclohexyl]-N,N-dimethylurea (Compound 1)

1000 tablets each weighing 200 mg were prepared according to the formulation shown in the table below.

| Composition | Amount (g) |
| --- | --- |
| Compound 1(active ingredient; prepared in Example 4) | 20.0 |
| Lactose | 126.0 |
| Microcrystalline Cellulose | 42.0 |
| Hydroxypropylmethyl Cellulose | 4.0 |
| Sodium Hydroxyethyl Starch | 6.0 |
| Magnesium Stearate | 2.0 |

The preparation method comprising: the active ingredient, lactose, microcrystalline cellulose and sodium hydroxyethyl starch were mixed and added to a high-shear wet granulator, stirring well at a certain rotating speed. Afterwards, 50.0 g of an aqueous solution of hydroxypropylmethylcellulose was added to the mixture to make it into appropriate granules under high-speed shearing conditions. The wet granules then were dried over a fluidized bed, and the resulting dried granules were uniformly mixed with the magnesium stearate and then compressed into tablets.

EXAMPLE 11

Preparation of an oral suspension of N'-[trans-4-[2-[4-(benzo[b]thiophene)-7-piperazinyl]ethyl]cyclohexyl]-N,N-dimethylurea (Compound 1)

1000 bottles each containing 5 ml (10 mg/ml as per specification) were prepared according to the formulation shown in the table below.

| Composition | Amount (g) |
| --- | --- |
| Compound 1(active ingredient; prepared in Example 4) | 50.0 |
| water | 3500.0 |
| Polyethylene Glycol | 50.0 |
| Sorbitol | 500.0 |
| Microcrystalline Cellulose | 25.0 |
| Xanthan Gum | 5.0 |
| Methyl p-Hydroxybenzoate | 1.25 |
| Ethyl p-Hydroxybenzoate | 1.25 |
| Citrate | Adjusting pH to 4-8 |

The preparation method comprising: methyl p-hydroxybenzoate and ethyl p-hydroxybenzoate were dissolved in hot water and then cooled to room temperature (25° C.±2° C.). Then, sorbitol, polyethylene glycol, xanthan gum, citrate, the compound 1 with an average particle size of 30 μm and microcrystalline cellulose were successively added, and stirred well to give an oral suspension.

EXAMPLE 12

Pharmacological Test
I. In Vitro Test on Biological Activity of the Cyclohexane Derivative of the Present Invention.

This test was carried out according to the dopamine $D_2/D_3$ receptor binding assay and the $5-HT_{1A}$ receptor binding assay described in Jiangsu Hengyi Pharmaceutical Co., Ltd.'s Patent CN 103130737 A. IC50 values were calculated from concentration-dependent reactions using a non-linear analysis program. Ki values were calculated from IC50 values by using Cheng-Prussoff equation, i.e. $Ki=IC_{50}/(1+[L]/KD)$, wherein Ki is the affinity of the drug to the receptor; L is the concentration of the compound to be tested; and KD is the affinity of radioligand to the receptor.

(I) Dopamine $D_2$ Receptor Binding Assay
i. Materials
a. Transfection of $D_2$ Receptor Cells: by using calcium phosphate method, HEK293 cells were transfected with a plasmid vector containing the $D_2$ receptor protein gene. The transfected cells were cultured in a culture solution containing G418, followed by a selection of monoclonal cell and radioligand binding assay, finally obtaining a stable cell line with stable expression of $D_2$ receptor protein.
b. Materials for receptor binding assay: isotope ligand [$^3$H] Spiperone (113.0 Ci/mmol); available from Sigma-Aldrich Company; (+) spiperone, available from RBI company; GF/B glass fiber filter paper, available from Whatman Company; Tris imported and packaged; PPO, POPOP, available from Shanghai Reagent Chemical Company; lipid-soluble scintillation solution; and Beckman LS-6500 Multi-function Liquid Scintillation Counter.

ii. Test Method
a. Treatment of cells: HEK-293 cells were infected with various recombinant viruses of the above genes, respectively, and the receptor proteins were highly expressed on the membranes after 48-72 hours. The cells were centrifuged at 1000 rpm for 5 minutes. The culture solution was discarded, and the cells were collected and stored in a refrigerator at −20° C. for standby. The cells were resuspended with Tris-HCl buffer (pH=7.5) when tested.
b. Competitive binding assay for receptor The compound to be tested and the radio ligand, both 20 μL, and 160 μL of receptor proteins were added to the reaction test tubes to achieve a final concentration of 10 μmol/L for each of the compound to be tested and positive control, incubated in a water bath of 30° C. for 50 minutes and immediately transferred to an ice bath to terminate the reaction; placed on a Millipore cell sample collector, filtered by suction rapidly through a GF/C glass fiber filter, and eluted with 3 mL of eluent (50 mM Tris-HCl, pH7.5) for three times and dried with microwave for 5-6 minutes. The filter paper was transferred into a 0.5 mL centrifuge tube to which 500 μL of lipid-soluble scintillation solution was added, and settled away from light for more than 30 minutes. The radioactive intensity was determined by counting. The concentration of the compound was 10 μmol/L, and inhibition rate (%) of each compound to the binding of isotope ligands was calculated according to the following equation:

Inhibition rate (I%)=(total binding tube cpm−compound cpm)/(total binding tube cpm—non-specific binding tube cpm)×100%.

(II) Dopamine $D_3$ Receptor Binding Assay

The concentration of the compound was 10 μmol/L, and the assay was performed according to the method described in Journal of Pharmacology and Experimental Therapeutics 2010, 333 (1): 328.

(III) $5-HT_{1A}$ Receptor Binding Assay
i. Materials $5-HT_{1A}$ receptor isotope ligand [$^3$H] 8-OH-DPAT (available from PE Company); (+)5-hydroxytrptamine (available from Sigma Company); GF/B glass fiber filter paper (available from Whatman Company); lipid-soluble scintillation solution: PPO, POPOP (available from Shanghai Chemical Reagent Company); toluene (from Sinopharm Chemical Reagent Co., Ltd.); Tris imported and packaged.

Treatment of cells: HEK-293 cells which stably express the $5-HT_{1A}$ receptor by gene recombination were cultured in DMEM+10% serum solution for 3-5 days and then collected with PBS. The cells were centrifuged at 3000 rpm and −4° C. for 10 minutes. Afterwards, the supernate was discarded, and the cells were collected and stored in a refrigerator at −80° C. The cells were resuspended with $D_1$ Binding Buffer (pH 7.4) when tested.

ii. Test Method

Inhibition rate of each compound of 10 umol/L to the binding of [$^3$H]8-OH-DPAT and the $5-HT_{1A}$ receptor was determined by a general selection.

The experimental data is shown in Table 1.

TABLE 1

Binding Assay of Compounds to $D_2$ and $D_3$ Receptors and Affinity to 5-$HT_{1A}$ Receptor (Ki: nmol)

| Compounds | $D_2$ | $D_3$ | 5-$HT_{1A}$ |
|---|---|---|---|
| 2 | >1000 | 0.06 | 3.85 |
| 3 | 978.2 | 0.07 | 3.72 |
| 1 | >1000 | 0.06 | 3.96 |
| 5 | 1.3 | 0.29 | 4.12 |

TABLE 1-continued

Binding Assay of Compounds to $D_2$ and $D_3$ Receptors and Affinity to 5-$HT_{1A}$ Receptor (Ki: nmol)

| Compounds | $D_2$ | $D_3$ | 5-$HT_{1A}$ |
|---|---|---|---|
| 6 | 250.9 | 0.57 | 22.83 |
| 7 | >1000 | 0.15 | 3.65 |

Conclusion: it can be seen from the experimental results in Table 1 that the series of compounds of the present invention have a strong affinity to $D_3$ and a very weak affinity to $D_2$ with nearly ten thousand folds difference between them, demonstrating that the series of compounds have high selectivity to $D_2/D_3$ receptors and reduce side effects when selecting $D_2$ receptor. Further, the compounds show relatively strong affinity to 5-$HT_{1A}$ receptor and act on a wide spectrum of neuropsychiatric diseases.

EXAMPLE 13

In Vivo Anti-Schizophrenic Activity Assay of the Cyclohexane Derivatives of the Present Invention I. MK-801 Model (I) Modeling of MK-801-Induced Schizophrenia in Mice 100 Sprague-Dawley rats (provided by Shanghai Lake Experimental Animal Co., Ltd.), all males, were randomly divided into 10 groups according to body weights: blank control, MK-801 model control, the cyclohexane derivatives $C_1$ to $C_8$ (corresponding to the compound 1 to the compound 7 and compound 14; 0.3 mg/kg) and Cariprazine positive control (prepared according to the method described in Patent CN103130737A; 0.3 mg/kg). Each rat was placed in a soundproof box for 30 minutes on the day before the test to adapt. On the next day, each rat was administrated with the respective test compounds, and after 30 minutes, administrated intraperitoneally with a 0.3 mg/kg MK-801 solution at 5.0 mL/kg body weight of the rat to build a model of MK-801-induced schizophrenia in mice.

Administration: the rats in the present cyclohexane derivatives and the cariprazine positive control groups were orally administered (i.g.), while the MK-801 model control group was administered intraperitoneally.

(II) Observation of Open Field Running Behavior

Mice were administered with MK-801 and then immediately placed in the soundproof box. The total distances of motion of mice within 2.5 hours were observed and recorded.

Improvement rate=(total distance of model control−total distance of administration)/(total distance of model control)×100%.

(III) Statistical Method

All the data was expressed with $\bar{x}\pm SD$ and processed by SPSS17.0 software statistical package. T-test and one-way analysis of variance were performed to compare the mean of two samples, with $P<0.05$ as significant difference.

(IV) Results

The results specifically are shown in Table 2 below.

TABLE 2

Effect of Single Oral Administration of the Cyclohexane Derivatives on the Total Distance of Open Field Motion in MK-801-Induced Schizophrenia in Mice Model
($\bar{x} \pm SD$)

| Groups | Number of Rats | Dosage (mg/kg) | Total Distance within 61-150 minutes (m) | Improvement Rate (%) |
|---|---|---|---|---|
| Blank Control | 10 | — | — | — |
| MK-801Model Control | 10 | 0.3 mg/kg | 309.78 ± 39.1 | — |
| Cariprazine Positive Control | 10 | 0.3 mg/kg | 168.25 ± 26.9**** | 45.69 |
| C1 (Compound 1) | 10 | 0.3 mg/kg | 73.09 ± 11.7**** | 76.41 |
| C2 (Compound 2) | 10 | 0.3 mg/kg | 46.95 ± 10.3**** | 84.84 |
| C3 (Compound 3) | 10 | 0.3 mg/kg | 63.79 ± 10.8**** | 79.41 |
| C4 (Compound 4) | 10 | 0.3 mg/kg | 232.18 ± 20.3* | 25.05 |
| C5 (Compound 5) | 10 | 0.3 mg/kg | 5.43 ± 1.7**** | 98.25 |
| C6 (Compound 6) | 10 | 0.3 mg/kg | 171.78 ± 13.0* | 12.27 |
| C7 (Compound 7) | 10 | 0.3 mg/kg | 160.82 ± 12.91* | 48.09 |
| C8 (Compound 14) | 10 | 0.3 mg/kg | 150.28 ± 11.70* | 51.49 |

The results in Table 2 show that the cariprazine positive control and the cyclohexane derivatives (Compound 1 to Compound 7) of the present invention have decreased the total distances of the rats within 150 minutes as compared with the MK-801 model control. Wherein *$P<0.05$, ****$P<0.0001$.

These results demonstrate that:
i. compared with the blank control, the distance of the open-field motion of MK-801 model control has increased significantly, indicating that MK-801 may causes schizophrenia in mice;
ii. compared with the MK-801 model control, and the cariprazine positive control has significantly inhibited the high spontaneous activity of MK-801-induced rats ($P<0.0001$) at a dose of 0.3 mg/kg; the cyclohexane derivatives, Compounds 1, 2, 3 and 5 of the present invention can significantly inhibit the high spontaneous activity of MK-801-induced rats ($P<0.0001$) at a dose of 0.3 mg/kg, and the cyclohexane derivatives, Compounds 6, 7 and 14 of the present invention also have significantly inhibited the high spontaneous activity of MK-801-induced rats ($P<0.05$) at a dose of 0.3 mg/kg, which are comparable with the cariprazine positive control. Since the MK-801-induced open-field motion model is closely related to the symptoms of schizophrenia, it is indicated that the cyclohexane derivative series of the present invention have a significant effect on schizophrenia.

EXAMPLE 14

Acute Toxicity Assay of the Cyclohexane Derivatives of the Present Invention

ICR mice orally administered with the compounds of the present invention were evaluated and their toxicity symptoms after oral administration were observed, as well as the mortality, which was calculated by Bliss method, thus the acute toxicities were compared.

Experimental Program
i. Preparation of solvent: Tween-80 of an appropriate amount was diluted with deionized water to a concentration of 5% (g/v) Tween-80.
ii. Formulations for administration: test samples were weighed as required, respectively, and made into suspensions with 5% the Tween-80 solution to achieve concentrations of 0.94, 1.88, 3.75, 7.5, 15, 30 and 60 mg/mL, respectively (equivalent to 18.75, 37.5, 150, 300, 600 and 1200 mg/kg, respectively).
iii. Administration: the test compound and solvent medium control groups (0.5% Tween-80) were administered orally.

Observation of general symptoms: Day 1: rats were observed at about 10 minutes, 0.5, 2, 4 and 6 hours after the first administration, respectively; Days 2-6, mice were observed twice a day, once in the morning and once in the afternoon. Observations include but are not limited to: general condition, behavior, gait, eyes, mouth, nose, gastrointestinal tract, skin and hair and urogenital tract.

The experimental results are shown in Table 4.

TABLE 4

Acute Toxicity of Single Oral Administration of Compounds

| Compounds | LD$_{50}$ (mg/Kg) |
|---|---|
| | 1100 mg/KG |

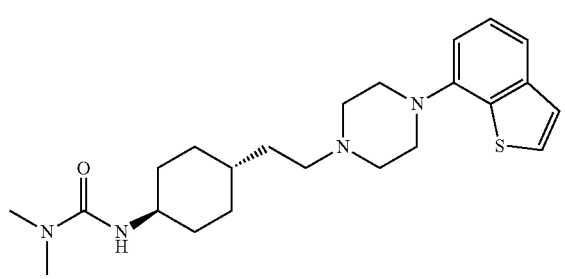

TABLE 4-continued

Acute Toxicity of Single Oral Administration of Compounds

| Compounds | LD$_{50}$ (mg/Kg) |
|---|---|
| 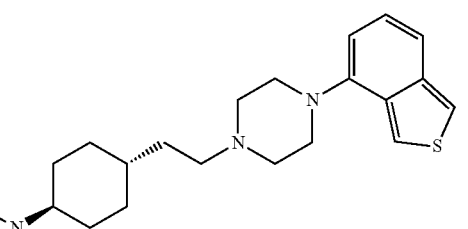 3 | 1050 mg/KG |
| 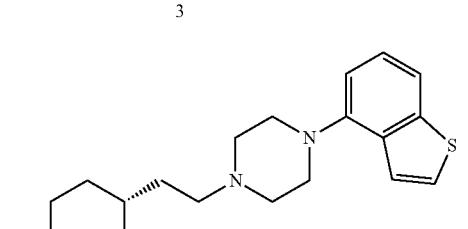 1 | 1080 mg/KG |

Conclusion: the acute toxicity of the cyclohexane derivatives of the present invention is far lower than that of the cariprazine positive control (RGH-188, 75.3 mg/kg), showing good safety.

What is claimed is:

1. A compound shown by the formula IB:

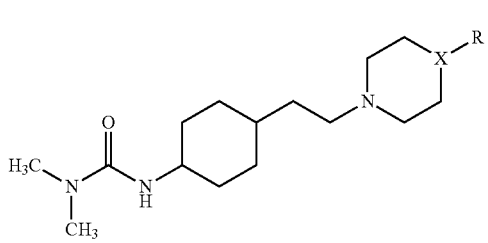

or a pharmaceutically acceptable salt or stereoisomer thereof,
wherein:
X is N or CH; and
R is

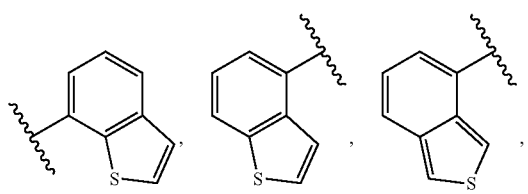

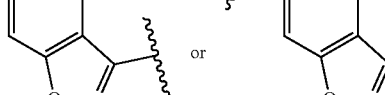

where R is optionally substituted with one or more substituents selected from the group consisting of F, Cl, Br, I and C$_1$-C$_6$ alkyl; and further
where the C$_1$-C$_6$ alkyl is optionally substituted with one or more substituents selected from the group consisting of F, Cl, Br and I.

2. The compound according to claim 1, or a pharmaceutically acceptable salt or stereoisomer thereof, wherein R is substituted with one C$_1$-C$_4$ alkyl, where the C$_1$-C$_4$ alkyl is substituted with one or more F.

3. The compound according to claim 1, or a pharmaceutically acceptable salt or stereoisomer thereof, wherein the pharmaceutically acceptable salt is an acid addition salt formed with an acid selected from the group consisting of hydrochloric acid, sulfuric acid, nitric acid, phosphoric acid, formic acid, acetic acid, oxalic acid, malonic acid, maleic acid, fumaric acid, succinic acid and benzoic acid.

4. The compound according to claim 1, or a pharmaceutically acceptable salt or stereoisomer thereof, wherein the stereoisomer is the cis-stereoisomer or the trans-stereoisomer.

5. The compound according to claim 1, or a pharmaceutically acceptable salt or stereoisomer thereof, wherein the compound is selected from the group consisting of:

N'-[trans-4-[2-[4-(benzo[b]thiophene)-7-piperazinyl]ethyl]cyclohexyl]-N,N-dimethylurea, compound 1;

N'-[trans-4-[2-[7-(benzo[b]thiophene)-7-piperazinyl]ethyl]cyclohexyl]-N,N-dimethylurea, compound 2;

N'-[trans-4-[2-[4-(benzo[c]thiophene)-7-piperazinyl]ethyl]cyclohexyl]-N,N-dimethylurea, compound 3;

N'-[trans-4-[2-[4-(6-fluorobenzo[d]isoxazol)-3-piperazinyl]ethyl]cyclohexyl]-N,N-dimethylurea, compound 5;

N'-[trans-4-[2-[4-(3-chlorobenzo[d]isoxazol)-6-piperazinyl]ethyl]cyclohexyl]-N,N-dimethylurea, compound 6;

N'-[trans-4-[2-[4-(6-fluorobenzo[d]isoxazol)-3-piperidinyl]ethyl]cyclohexyl]-N,N-dimethylurea, compound 7

N'-[trans-4-[2-[4-(benzo[b]thiophene)-7-piperidinyl]ethyl]cyclohexyl]-N,N-dimethylurea, compound 8;

N'-[trans-4-[2-[7-(benzo[b]thiophene)-7-piperidinyl]ethyl]cyclohexyl]-N,N-dimethylurea, compound 9;

N'-[trans-4-[2-[4-(benzo[c]thiophene)-7-piperidinyl]ethyl]cyclohexyl]-N,N-dimethylurea, compound 10;

N'-[trans-4-[2-[4-(benzo[d]isothiazolyl)-3-piperidinyl]ethyl]cyclohexyl]-N,N-dimethylurea, compound 11;

N'-[trans-4-[2-[4-(3-chlorobenzo[d]isoxazol)-6-piperidinyl]ethyl]cyclohexyl]-N,N-dimethylurea, compound 12;

N'-[trans-4-[2-[4-(3-methylbenzo[d]isoxazol)-6-piperazinyl]ethyl]cyclohexyl]-N,N-dimethylurea, compound 13; and N'-[trans-4-[2-[4-(6-methylbenzo[d]isoxazol)-4-piperazinyl]ethyl]cyclohexyl]-N,N-dimethylurea, compound 14.

6. A pharmaceutical composition comprising as an active ingredient a compound according to claim 1, or a pharmaceutically acceptable salt or stereoisomer thereof, and a pharmaceutically acceptable excipient.

7. The pharmaceutical composition according to claim 6, wherein the pharmaceutical composition is a solid or a liquid preparation for oral, gastrointestinal, buccal, sublingual, nasal, rectal or transdermal administration.

8. The pharmaceutical composition according to claim 7, wherein the pharmaceutical composition is a solid tablet.

9. The pharmaceutical composition according to claim 8, wherein the compound in the solid tablet is N'-[trans-4-[2-[4-(benzo[b]thiophene)-7-piperazinyl]ethyl]cyclohexyl]-N,N-dimethylurea.

10. The pharmaceutical composition according to claim 7, wherein the pharmaceutical composition is a suspension.

11. The pharmaceutical composition according to claim 10, wherein the compound in the suspension is N'-[trans-4-[2-[4-(benzo[b]thiophene)-7-piperazinyl]ethyl]cyclohexyl]-N,N-dimethylurea.

12. A method for inhibiting dopamine D2 receptor binding activity in a patient, comprising administering to a patient in need thereof a therapeutically effective amount of the pharmaceutical composition according to claim 6.

13. The method according to claim 12, wherein the patient suffers from one or more disorders selected from the group consisting of a phobia, a mental disorder, a mood disorder, a cognitive disorder and an obsessive-compulsive disorder.

14. The method according to claim 13, wherein the mental disorder, mood disorder or cognitive disorder is selected from the group consisting of mental confusion, schizophrenia, depression, anxiety, dysphrenia and a bipolar disorder.

15. A method for inhibiting 5-hydroxytryptamine 1A receptor binding activity in a patient, comprising administering to a patient in need thereof a therapeutically effective amount of the pharmaceutical composition according to claim 6.

16. The method according to claim 15, wherein the patient suffers from one or more disorders selected from the group consisting of a phobia, a mental disorder, a mood disorder, a cognitive disorder and an obsessive-compulsive disorder.

17. The method according to claim 16, wherein the mental disorder, mood disorder or cognitive disorder is selected from the group consisting of mental confusion, schizophrenia, depression, anxiety, dysphrenia and a bipolar disorder.

18. A process for preparing a compound according to claim 1 shown by the formula IB:

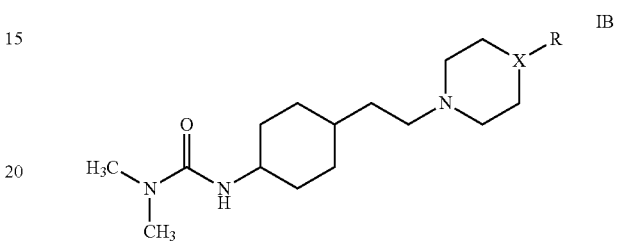

wherein the process comprises:

reacting a compound of the formula II:

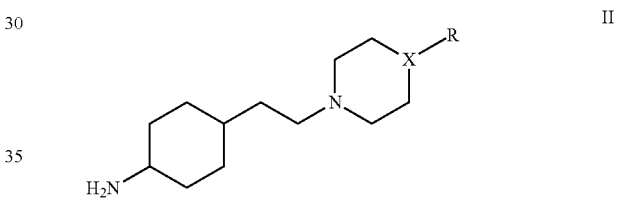

wherein:

X is N or CH: and

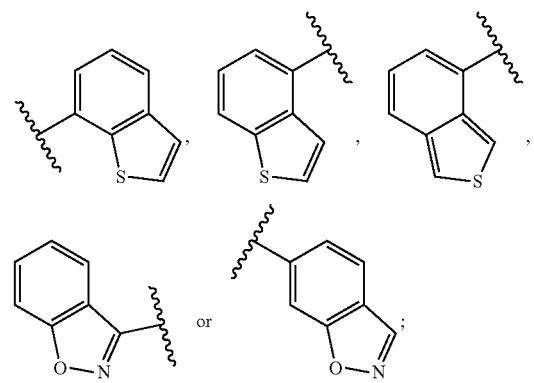

R is where R is optionally substituted with one or more substituents selected from the group consisting of F, Cl, Br, I and $C_1$-$C_6$ alkyl; and further where the $C_1$-$C_6$ alkyl is optionally substituted with one or more substituents selected from the group consisting of F, Cl, Br and I;

with a compound of the formula III:

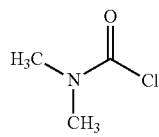

in the presence of a base selected from the group consisting of triethylamine, diisopropylethylamine, pyridine, sodium carbonate, potassium carbonate, sodium bicarbonate and potassium bicarbonate, to provide the compound according to claim 1 shown by the formula IB above.

19. A process for preparing the pharmaceutical composition according to claim 6, wherein the process comprises admixing a pharmaceutically acceptable excipient with the compound according to claim 1, or a pharmaceutically acceptable salt or stereoisomer thereof.

20. A compound shown by the formula I:

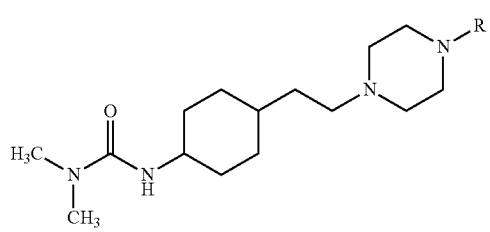

or a pharmaceutically acceptable salt or stereoisomer thereof,
wherein:
R is

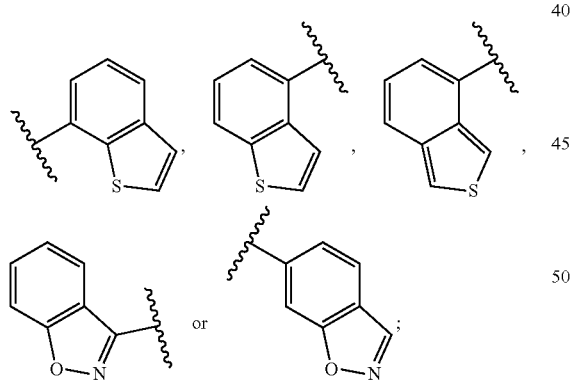

where R is optionally substituted with one or more substituents selected from the group consisting of F, Cl, Br, I and $C_1$-$C_6$ alkyl; and further
where the $C_1$-$C_6$ alkyl is optionally substituted with one or more substituents selected from the group consisting of F, Cl, Br and I.

21. The compound according to claim 20, or a pharmaceutically acceptable salt or stereoisomer thereof, wherein R is substituted with one $C_1$-$C_4$ alkyl, where the $C_1$-$C_4$ alkyl is substituted with one or more F.

22. The compound according to claim 20, or a pharmaceutically acceptable salt or stereoisomer thereof, wherein the pharmaceutically acceptable salt is an acid addition salt formed with an acid selected from the group consisting of hydrochloric acid, sulfuric acid, nitric acid, phosphoric acid, formic acid, acetic acid, oxalic acid, malonic acid, maleic acid, fumaric acid, succinic acid and benzoic acid.

23. The compound according to claim 20, or a pharmaceutically acceptable salt or stereoisomer thereof, wherein the stereoisomer is the trans-stereoisomer.

24. The compound according to claim 20, or a pharmaceutically acceptable salt or stereoisomer thereof, wherein the compound is selected from the group consisting of:
N'-[trans-4-[2-[4-(benzo[b]thiophene)-7-piperazinyl]ethyl]cyclohexyl]-N,N-dimethylurea, compound 1;
N'-[trans-4-[2-[7-(benzo[b]thiophene)-7-piperazinyl]ethyl]cyclohexyl]-N,N-dimethylurea, compound 2;
N'-[trans-4-[2-[4-(benzo[c]thiophene)-7-piperazinyl]ethyl]cyclohexyl]-N,N-dimethylurea, compound 3;
N'-[trans-4-[2-[4-(6-fluorobenzo[d]isoxazol)-3-piperazinyl]ethyl]cyclohexyl]-N,N-dimethylurea, compound 5;
N'-[trans-4-[2-[4-(3-chlorobenzo[d]isoxazol)-6-piperazinyl]ethyl]cyclohexyl]-N,N-dimethylurea, compound 6;
N'-[trans-4-[2-[4-(3-methylbenzo[d]isoxazol)-6-piperazinyl]ethyl]cyclohexyl]-N,N-dimethylurea, compound 13; and
N'-[trans-4-[2-[4-(6-methylbenzo[d]isoxazol)-4-piperazinyl]ethyl]cyclohexyl]-N,N-dimethylurea, compound 14.

25. A pharmaceutical composition comprising as an active ingredient a compound according to claim 20, or a pharmaceutically acceptable salt or stereoisomer thereof, and a pharmaceutically acceptable excipient.

26. A process for preparing a compound according to claim 20 shown by the formula I:

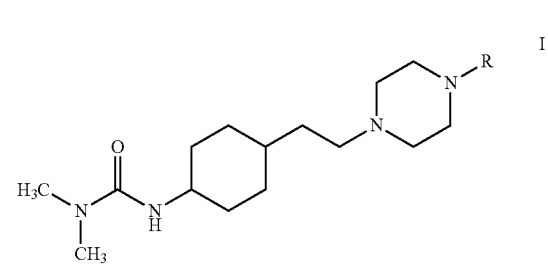

wherein the process comprises:
reacting a compound of the formula II:

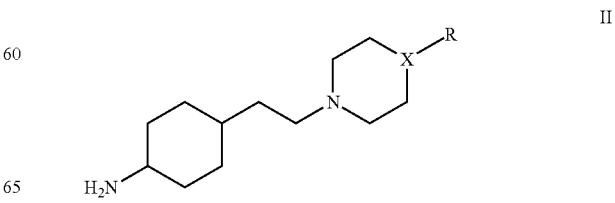

wherein:
R is

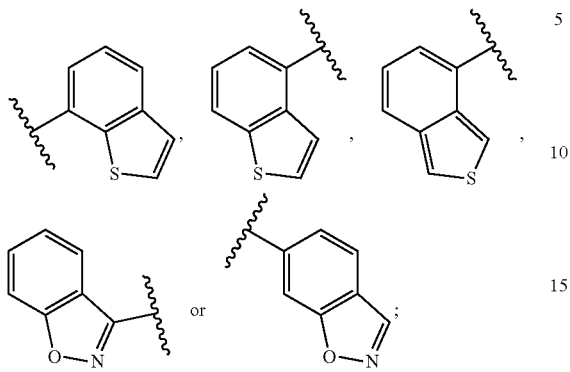

where R is optionally substituted with one or more substituents selected from the group consisting of F, Cl, Br, I and $C_1$-$C_6$ alkyl; and further
where the $C_1$-$C_6$ alkyl is optionally substituted with one or more substituents selected from the group consisting of F, Cl, Br and I;

with a compound of the formula III:

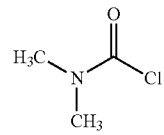

in the presence of a base selected from the group consisting of triethylamine, diisopropylethylamine, pyridine, sodium carbonate, potassium carbonate, sodium bicarbonate and potassium bicarbonate, to provide the compound according to claim 20 shown by the formula I above.

27. A process for preparing the pharmaceutical composition according to claim 25, wherein the process comprises admixing a pharmaceutically acceptable excipient with the compound according to claim 20, or a pharmaceutically acceptable salt or stereoisomer thereof.

* * * * *